United States Patent [19]

Wang et al.

[11] Patent Number: 4,713,068
[45] Date of Patent: Dec. 15, 1987

[54] BREATHABLE CLOTHLIKE BARRIER HAVING CONTROLLED STRUCTURE DEFENSIVE COMPOSITE

[75] Inventors: Kenneth Y. Wang, Roswell; Richard S. Yeo, Dunwoody, both of Ga.

[73] Assignee: Kimberly-Clark Corporation, Neenah, Wis.

[21] Appl. No.: 925,425

[22] Filed: Oct. 31, 1986

[51] Int. Cl.$^4$ .............................................. A61F 13/16
[52] U.S. Cl. ................................ 604/366; 604/378; 428/284; 428/286; 428/290; 428/297; 428/298; 428/340; 428/903; 428/913
[58] Field of Search ............... 428/903, 913, 284, 286, 428/290, 297, 298, 340; 604/366, 378

[56] References Cited

U.S. PATENT DOCUMENTS

| | | | |
|---|---|---|---|
| 3,016,599 | 1/1962 | Perry, Jr. ........................ | 28/78 |
| 3,156,242 | 11/1964 | Crowe ........................... | 128/296 |
| 3,203,419 | 1/1963 | Joa .............................. | 128/290 |
| 3,253,715 | 5/1966 | Painter et al. .................. | 210/504 |
| 3,426,754 | 2/1969 | Bierenbaum et al. ............... | 128/156 |
| 3,518,041 | 6/1970 | Brelich ......................... | 8/115.7 |
| 3,590,585 | 7/1971 | DeWinter ........................ | 61/5 |
| 3,597,307 | 8/1971 | Paulusma et al. ................. | 161/170 |
| 3,612,054 | 10/1971 | Matsuda et al. .................. | 128/287 |
| 3,640,829 | 2/1972 | Elton ........................... | 161/159 |
| 3,679,538 | 7/1972 | Druin et al. .................... | 156/196 |
| 3,692,618 | 9/1972 | Dorschner et al. ................ | 28/72 |
| 3,704,198 | 11/1972 | Prentice ........................ | 161/170 |

(List continued on next page.)

FOREIGN PATENT DOCUMENTS

| | | |
|---|---|---|
| 0105629 | 4/1984 | European Pat. Off. . |
| 0141592 | 5/1985 | European Pat. Off. . |
| 0184392 | 11/1986 | European Pat. Off. . |
| 3417909 | 11/1985 | Fed. Rep. of Germany |
| 57-142323 | 9/1982 | Japan . |
| 2103537 | 2/1983 | United Kingdom . |
| 2115702 | 10/1985 | United Kingdom . |

OTHER PUBLICATIONS

MONO-SOL 1-000 Series Hot Water Soluble Plastic Film Data Sheet (MONO-SOL Division, Chris Craft Industries, Inc., Gary, Ind. 46403).

"Resins, Water-Soluble", A Chapter from Kirk-Othmer Encyclopedia of Chemical Technology, Third Edition, vol. 20, John Wiley and Sons, New York, 1982, pp. 207-230.

(List continued on next page.)

Primary Examiner—James J. Bell
Attorney, Agent, or Firm—William E. Maycock

[57] ABSTRACT

A breathable clothlike barrier which includes a defensive composite having at least two layers:

A. a first layer which is a clothlike porous substrate having a first side and a second side, in which:
   the first layer has a nominal basis weight of at least about 10 g/m$^2$;
   the fibers comprising the first layer have an average fiber diameter in the range of from about 0.01 to about 10 microns; and
   each of substantially all of the pores at the surface of the first side of the first layer has a cross-sectional area of from about $6 \times 10^{-16}$ m$^2$ to about $2 \times 10^{-9}$ m$^2$; and B. a second layer joined to the first side of the first layer, which second layer is a continuous film of a poly(vinyl alcohol), in which:
   the film is not microporous in that it is substantially free of voids which connect the two surfaces of the film; and
   the film has an average thickness of (a) from about 3 to about 25 microns when the basis weight of the first layer is at least about 20 g/m$^2$ or (b) from about 8 to about 25 microns when the basis weight of the first layer is from about 10 to less than about 20 g/m$^2$;

in which the first layer side of the second layer is intimately comingled with at least some of the fibers at the surface of the first side of the first layer, and the defensive composite has a water vapor transmission rate at 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

69 Claims, 15 Drawing Figures

U.S. PATENT DOCUMENTS

| | | | |
|---|---|---|---|
| 3,755,527 | 8/1973 | Keller et al. | 264/210 F |
| 3,843,761 | 10/1984 | Bierenbaum et al. | 264/41 |
| 3,849,241 | 11/1974 | Butin et al. | 161/169 |
| 3,869,310 | 3/1975 | Fukushima et al. | 264/123 |
| 3,870,593 | 3/1975 | Elton et al. | 161/402 |
| 3,891,487 | 6/1975 | Hoey | 156/78 |
| 3,932,682 | 1/1976 | Loft et al. | 428/296 |
| 4,006,052 | 2/1977 | Wang | 156/280 |
| 4,100,324 | 7/1978 | Anderson et al. | 428/288 |
| 4,178,271 | 12/1979 | Busch et al. | 260/17 R |
| 4,197,148 | 4/1980 | Shinomura | 156/79 |
| 4,197,371 | 4/1980 | Holst et al. | 521/84 |
| 4,226,906 | 10/1980 | Jacob | 428/283 |
| 4,247,498 | 1/1981 | Castro | 264/41 |
| 4,257,997 | 3/1981 | Soehngen et al. | 264/145 |
| 4,289,832 | 9/1981 | Schwarz | 428/910 |
| 4,304,812 | 12/1981 | Perkins | 428/247 |
| 4,308,303 | 12/1981 | Mastroianni et al. | 428/90 |
| 4,347,844 | 9/1982 | Ohki et al. | 128/287 |
| 4,384,023 | 5/1983 | Okamura et al. | 428/338 |
| 4,415,617 | 11/1983 | D'Elia | 428/86 |
| 4,430,278 | 2/1984 | Jones, Sr. | 264/22 |
| 4,452,845 | 6/1984 | Lloyd et al. | 428/220 |
| 4,454,191 | 6/1984 | von Blucher et al. | 428/244 |
| 4,472,328 | 9/1984 | Sugimoto et al. | 264/41 |
| 4,519,909 | 5/1985 | Castro | 264/41 |
| 4,539,256 | 9/1985 | Shipman | 156/229 |
| 4,560,611 | 12/1985 | Naka et al. | 428/266 |
| 4,578,069 | 3/1986 | Whitehead et al. | 604/370 |
| 4,591,523 | 5/1986 | Thompson | 428/131 |
| 4,595,001 | 6/1986 | Potter et al. | 128/156 |
| 4,603,077 | 7/1986 | Fujimoto et al. | 428/289 |
| 4,608,111 | 8/1986 | Hume, III et al. | 156/306.6 |
| 4,613,544 | 9/1986 | Burleigh | 428/422 |

OTHER PUBLICATIONS

"Vinyl Polymers (Poly(Vinyl Alcohol))," A Chapter in Kirk-Othmer Encyclopedia of Chemical Technology, Third Edition, vol. 23, John Wiley and Sons, New York, 1983, pp. 848-865.

VINOL Poly(Vinyl Alcohol) Product Line brochure, Air Products and Chemicals, Inc., Polymer Chemicals, Allentown, Pa. 18105.

VINOL Poly(Vinyl Alcohol) Product Bulletin, Air Products and Chemicals, Inc., Polymer Chemicals, Allentown, Pa. 18105.

BREATHABLE CLOTHLIKE BARRIER HAVING CONTROLLED STRUCTURE DEFENSIVE COMPOSITE

CROSS-REFERENCES TO RELATED APPLICATIONS

A breathable barrier which comprises a porous sheet coated with poly(vinyl alcohol) or laminated to a poly(vinyl alcohol) film is described and claimed in copending and commonly assigned application Ser. No. 926,033, entitled BREATHABLE BARRIER, filed of even date in the names of Richard S. Yeo and Daniel K. Schiffer. The use of a continuous film of a poly(vinyl alcohol) joined to a porous substrate is described and claimed in copending and commonly assigned application Ser. No. 925,446, entitled BAFFLE HAVING ZONED WATER VAPOR PERMEABILITY, filed of even date in the names of Kenneth Y. Wang and Richard S. Yeo. Finally, a barrier having at least three layers, one of which is a continuous film of poly(vinyl alcohol), is described and claimed in copending and commonly assigned application Ser. No. 925,332, entitled BREATHABLE, MULTILAYER, CLOTHLIKE BARRIER, filed of even date in the names of Ralph V. Braun, Lance Garrett, Robert J. Phelan, and Richard S. Yeo.

BACKGROUND OF THE INVENTION

The present invention relates to a breathable clothlike barrier, i.e., a structure which is substantially impervious to liquid water but permeable by water vapor. More particularly, the present invention relates to a breathable clothlike barrier having a controlled structure defensive composite. Such barrier is especially well suited for use as an outer cover or baffle for such absorbent articles as disposable diapers, sanitary napkins, and incontinent pads.

Absorbent articles, especially disposable absorbent articles such as diapers, sanitary napkins, bedpads, incontinent pads, and the like are well known and important items of commerce. Such articles are capable of absorbing and retaining liquid discharges from the body. They typically have an outer cover or baffle of a liquid-impermeable plastic film, such as a polyethylene or polypropylene film, to prevent retained liquid from leaking from the article and soiling items of clothing, bedding, furniture, and the like.

Such liquid-impermeable film prevents, or at least minimizes, leakage by establishing a barrier to the passage of liquid from the absorbent article in situations where either the capacity of the absorbent article has been exceeded or the loading of the target zone exceeded the capacity of the absorbent article to wick liquid from the target zone to storage areas.

Such film, however, suffers from several disadvantages. Because the film is impermeable to both liquid and water vapor, the absorbent article feels hot when dry and clammy when wet. Such clammy state can cause irritation of the skin and even severe dermatological problems, such as diaper rash on infants wearing disposable diapers which have been left on too long. In fact, diaper rash can develop relatively quickly because of illness or changes in diet. In addition, the plastic film employed as the outer cover is severely lacking in aesthetic qualities, especially for such products as disposable diapers.

One proposal for the elimination of such disadvantages is the use of a breathable, liquid impermeable barrier, i.e., outer cover or baffle. As used herein, the term "breathable" means that the barrier is pervious to water vapor; that is, water vapor will pass through the barrier. While considerable progress has been made in the development of breathable films, such materials typically still are lacking in aesthetic qualities.

Various breathable outer covers or other materials are known. For example, U.S. Pat. No. 3,156,242 discloses a flexible absorbent sheet which is useful as a surgical dressing. The backing sheet or outer layer of the dressing is either air pervious by nature, such as a microporous film, or has had holes or slits formed in it. The example employed a perforated polyethylene film.

U.S. Pat. No. 3,426,754 teaches a breathable medical dressing. Such dressing comprises a backing having an open-celled structure, preferably coated with a continuous layer of a microporous pressure-sensitive adhesive. The backing employs a plastic film to which the desired properties have been imparted as a result of special processing conditions. The film typically can be prepared from polyolefins, polyacetals, polymethylene sulfide, polyethylene sulfide, polyphenylene oxide, polyamides, polyesters, and the like. The film possesses an open-celled structure, the voids of which are accessible to the outside surface by means of passageways which generally are under 5,000 Angstroms, e.g., from 100 to 5,000 Angstroms. In addition, such film has a final crystallinity of at least 40 percent.

A porous sheet and a process for making it are described in U.S. Pat. No. 4,347,844. The sheet is reported to be useful as a water-impermeable, vapor-permeable backing sheet for disposable diapers. The sheet contains a filler, the particles of which have been broken by the application of a compressive force to cause the formation of voids or spaces, i.e., micropores, which permit the passage of water vapor through the sheet while acting as a barrier to liquid water. The sheet apparently can be made of a nonfoamed thermoplastic resin, such as polyethylene and nylon. In addition, the patent suggests that the film can be of a composite of a polyethylene or nylon film and spunbonded polyethylene or polyester. The use of a spunbonded material alone does not appear to be within the scope of the disclosure.

Another type of microporous film is described in U.K. Patent No. GB 2,115,702B. The patent is directed toward an absorbent article, such as a disposable diaper or sanitary napkin, in which the article has a vapor-permeable, liquid-impermeable backing sheet. The backing sheet is composed of a film produced by mixing 100 parts by weight of a polyolefin resin, 28 to 200 parts by weight of a filler, and 10 to 70 parts by weight of a liquid or wax-like hydrocarbon polymer, molding the mixture to form a film, and then stretching the film laterally and/or longitudinally until it has a dimension of more than 1.2 times its original dimension in that direction, thereby resulting in the formation of fine pores in the film. Examples of polyolefins include polyethylene and polypropylene. A variety of fillers can be used, and examples of the hydrocarbon polymer include liquid polybutadienes. Liquid polybutenes, and hydrogenates of liquid polybutadienes, among which saturated polyhydroxy-substituted hydrocarbons obtained by hydrogenating hydroxy-terminated liquid polybutadienes are preferred. See also U.S. Pat. No. 3,870,593 which describes stretching a film containing finely divided particles of a nonhygroscopic inorganic salt, such as calcium carbonate, in order to obtain a microporous film. The microporous sheet material described in U.S. Pat. No. 3,640,829 also involves incorporating within the polymer an inorganic salt which is leached out to produce the micropores.

U.S. Pat. No. 4,591,523 relates to an apertured, macroscopically expanded, three-dimensional polymeric web exhibiting breathability and resistance to fluid transmission. The web is reported to have particular utility as a breathable barrier for a disposable diaper. The web preferably comprises a deeply drawn three-dimensional structure containing a multiplicity of debossments of macroscopic cross-section (i.e., visibly perceivable by the normal human eye at a perpendicular distance of about one foot), each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. These smaller apertures in each end wall are so spaced relative to all adjacent apertures in the end wall that the aqueous fluid menisci supported in the apertures do not contact one another.

Waterproof products capable of transmitting air and water vapor which have fabric-like aesthetic properties are described in U.S. Pat. No. 3,932,682. The products are made by spray-spinning filamentary material directly onto an open-celled microporous polymer film, such that thermal self-bonding occurs between the filamentary material and the film, or by spray-spinning the filamentary material in the same manner onto an elastic film, stretching the resulting product until an open-celled structure is produced in the film portion of the product and thereafter heating or heat setting the resulting product at substantially constant length to impart dimensional stability thereto. Polymers suitable for making the films appear to be those described in U.S. Pat. No. 3,426,754, discussed hereinabove. As already noted, the filamentary material is produced by spray-spinning, i.e., meltblowing, directly onto the film.

U.S. Pat. No. 4,308,303 describes a flocked, foam-coated, fibrous-reinforced, water vapor permeable barrier having the appearance of fabric and capable of filtering bacteria. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer. The film is rendered microporous by stretching a film which contains minute fracture sites or pore-nucleating agents such as finely divided filler and/or minute crystalline domains. The use of a finely divided, inorganic, water-insoluble, inert filler such as calcium carbonate having an average particle size of less than 3 microns is preferred.

U.S. Pat. No. 4,560,611 relates to a moisture-permeable, waterproof coated fabric. Briefly, a microporous polyurethane layer is formed on a base fabric which may be knitted, woven, nonwoven, or the like. The coating solution consists of a polar organic solvent solution containing 8 to 25 percent by weight of a polyurethane elastomer, 0.1 to 10 percent by weight of a water repellent agent, 0.2 to 3 percent by weight of a polyisocyanate, and 1 to 8 percent by weight of a nonionic surfactant. The water-repellent agent typically is a fluorine- or silicone-based material. The polyisocyanate usually will be any of the well known di- or triisocyanates. The polyurethane elastomer can be a polyester or polyether polyurethane.

A somewhat similar approach is described in European Patent Application No. 85308671.8, Publication No. 0 184 392 A2. A waterproof, moisture-vapor permeable unitary sheet metal comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough, thereby rendering the sheet material breathable. Preferably, the average pore size will be less than about 10 percent of the thickness of the matrix. By way of example, the average pore size for a matrix having a thickness of about 10 to 50 micrometers typically will be on the order of 1 to 5 micrometers or less. By contrast, the average pore size or opening of a woven fabric is about the same magnitude as its thickness. A matrix having too large a pore size will permit tha passage of water therethrough as hydrophilic material solidified therein will not sufficiently close the pores against the passage of liquid. The matrix can be prepared by known methods from any polymeric material which is substantially inpenetrable by water. Suitable polymeric materials include polyolefins, polyesters, polyamides, and the like. The preferred hydrophilic material is polyethylene oxide which preferably is polymerized with a polyisocyanate to give a polyurethane.

U.S. Pat. No. 4,197,371 discloses a water vapor absorbing and transmitting sheet material. The sheet material comprises a natural or synthetic rubber or a rubber-like polymer having uniformly incorporated therein particles of at least one swellable modified polymer. Examples of suitable swellable modified polymers include, among others, modified starches and celluloses. Apparently, such sheet materials are not suitable for use as an outer cover or baffle for a disposable absorbent product, e.g., a diaper or sanitary napkin. See also U.S. Pat. No. 4,178,271 which describes a similar sheet material based on a sheet-like structure of poly(vinyl chloride) or a copolymer of vinyl chloride.

U.S. Pat. No. 3,869,310 describes flexible sheet materials which are leather-like. Although the materials allegedly have improved physical properties, particular properties, such as water vapor permeability, are not discussed. The materials comprise a nonwoven fibrous mat and a polymeric impregnant which has a porous structure and is substantially not bonded to the fibers of the mat. The materials are obtained by preparing a nonwoven fibrous mat composed of fibers prepared from at least two different polymeric materials, impregnating the mat with a first liquid which is a solvent for one of the polymeric materials and a nonsolvent for the other polymeric materials, dissolving the fibers composed of the polymeric material which is soluble in the liquid, and coagulating the polymer solution resulting from the addition of the first liquid into a porous polymeric structure which is substantially not bonded to the undissolved fibers by the addition of a second liquid which is a nonsolvent for all of the polymeric materials originally present in the nonwoven fibrous mat but which is at least partially miscible with the first liquid.

The list of suitable polymeric materials which can be employed includes poly(vinyl alcohol), although the preferred combinations of polymeric materials apparently are nylon-6 and polystyrene, nylon-6 and polypropylene, poly(ethylene terephthalate) and polystyrene, poly(vinyl chloride) and polypropylene, nylon-6 and poly(vinyl acetate), and nylon-6 and a polyurethane elastomer. One example, however, involved the use of a nonwoven mat composed of fibers of poly(vinyl chloride) and poly(vinyl alcohol); the first liquid was N,N-dimethylformamide which is a solvent for poly(vinyl alcohol) but a nonsolvent for poly(vinyl chloride).

The use of poly(vinyl alcohol) as a binder for a nonwoven fabric is described in U.S. Pat. No. 3,518,041. The nonwoven fabric is composed of cellulosic fibers alone or in combination with other natural or synthetic fibers. The binder is a poly(vinyl alcohol) resin in film, powder, fiber, or other particulate form which is crosslinked in situ with formaldehyde. The binder is applied to the fabric as an aqueous solution or poly(vinyl alcohol) fibers may be incorporated into the fabric and activated by treating the fabric with water. The fabric then is treated with an aqueous solution of formaldehyde which contains a catalyst.

A disclosure somewhat similar to that of the above patent is found in U.S. Pat. No. 3,253,715 which describes boil-proof nonwoven filter media. The media are prepared by treating a multilayered nonwoven fabric with a binder which is an aqueous solution of poly(vinyl alcohol) and a polyacrylic acid or crosslinked polyacrylic acid.

It is interesting to note that, in contrast to U.S. Pat. Nos. 3,518,041 and 3,253,715, U.S. Pat. No. 3,590,585 describes a composite structure, useful as an artificial seaweed, which employs water-decomposable poly(vinyl alcohol) filaments to temporarily hold buoyant, water-resistant strands in place during handling, transporting, and installing of the product. Also of interest in this regard is U.S. Pat. No. 4,304,812 which describes the backcoating of an open-weave fabric. Prior to the backcoating step, a temporary protective coating is applied to the face of the fabric. After backcoating the fabric, the protective coating is removed with a solvent medium. Suitable protective coatings preferably are at least partially water soluble and include water-soluble poly(vinyl alcohol) or partially hydrolyzed poly(vinyl acetate.

U.S. Pat. No. 3,597,307 describes a supple sheet material which is composed of a fibrous nonwoven web and a polyurethane filler. The fibers of the web can be prepared from poly(vinyl alcohol) and the amount of the filler can be up to 30 percent by weight, based on the weight of the sheet material. Although the sheet material is stated to have a good water vapor pick-up value, it is not known if the material is permeable to water vapor. See also U.S. Pat. No. 4,006,052.

U.S. Pat. No. 3,891,487 discloses a decorative laminate which has a textile backing, a crushed, thermoset plastic foam bonded thereto, and a transparent polymeric film overlaying the foam. The film preferably is cast from a latex; suitable materials for preparing the latex include poly(vinyl alcohol). The film can be made breathable by mechanically foaming the latex before casting, mechanically puncturing the film, using chemical blowing agents, or dissolving or digesting out temporary fillers placed in the latex before it is cast. The textile backing apparently can be either woven or nonwoven. The decorative laminate is useful as, for example, a simulated oil painting, and clearly is not intended to be contacted by water.

Microporous coated fabrics are described in U.S. Pat. No. 4,226,906. Microporosity apparently results from the use of clustered microspheres. The microspheres may be synthetic or naturally occurring. If the former, they are prepared by bonding individual microspheres in a matrix which is insoluble in the coating composition; the bonding agent for such matrix can be, for example, poly(vinyl alcohol). However, the patent does not appear to teach the use of poly(vinyl alcohol) in the preparation of microporous coated fabrics when naturally occurring microspheres are used; in such case, the coating composition was based on poly(vinyl chloride) and the fabric was a nonwoven polyester.

U.S. Pat. No. 4,415,617 discloses a base fabric for the manufacture of embroidery and lace. The base fabric is a nonwoven web of poly(vinyl alcohol) fibers which has been processed in such a manner as to convert one surface of the web into a gas-permeable film comprising thermoplasticized and rehardened, flattened fibers and portions of fibers. The base fabric then can be dissolved away from embroidery stiched thereon by exposing the fabric to water at a temperature of about 100 degrees C.

U.S. Pat. No. 4,454,191 describes a waterproof and moisture-conducting fabric coated with a hydrophilic polymer. The fabric can be a woven, knit, felt, or nonwoven material which is composed of natural, synthetic, or mineral fibers. The fabric itself must be permeable to water vapor. The fabric is sealed with a hydrophilic polymer which is capable of absorbing, transporting, and releasing water molecules. Such capability results from the presence in the polymer of hydrophilic groups, such as hydroxy, amino, ether, and carboxy groups. Thus, suitable polymers include those prepared from hydroxyalkyl acrylates, the acrylic or methacrylic esters of polyalkylene oxides or polyalkylenimides, and the like. Other suitable polymers include modified vinyl alcohol resins, regenerated cellulose, a poly(vinyl chloride) having built-in monomers which have powerful hydrophilic groups, copolymerizates of vinyl chloride and vinyl acetate in which the acetate groups have been hydrolyzed to hydroxy groups, and polyurethanes having excess hydroxy or amino groups.

A somewhat related disclosure is found in German Published Patent Application No. 3417909 A1, which describes the use of a water-soluble poly(vinyl alcohol) film in the resorbent material of a sanitary pad. The film reportedly prevents soiling of clothing while permitting sanitary disposal of the used article. There appears to be no mention of the characteristics of the film or where and how the film is placed in the pad.

It perhaps should be mentioned that there is a relatively large body of literature on the preparation of microporous films, only a relatively small portion of which has been discussed hereinabove. While a detailed discussion of such body of literature is beyond the scope of this section, a limited number of additional, representative references perhaps should be mentioned for the sake of completeness. Such references include, by way of illustration only, U.S. Pat. Nos. 4,247,498, 4,519,909, 4,257,997, 4,452,845, 4,539,256, 3,843,761, 3,679,538, 4,430,278, 4,289,832, 4,384,023, 4,472,328, 4,197,148, U.K. Published Patent Application No. GB 2,103,537A, Japenese Published Patent Application No. 57-142323, and European Patent Application Nos. 84307198.6, Publication No. 0 141 592 A2, and 83305161.8, Publication No. 0 105 629 A2.

Finally, a more aesthetically pleasing barrier is described in U.S. Pat. No. 4,578,069. The barrier is a breathable baffle composite which is employed in the construction of a sanitary napkin. The baffle is formed by joining webs of a meltblown polyolefin and a spunbonded polyolefin, with the latter providing a surface for the adhesive which permits attachment of the napkin to an article of clothing.

Although various of the breathable barriers described above have proven useful in such absorbent articles as disposable diapers and santiary napkins, there still is a need for an effective breathable outer cover or baffle which has a clothlike feel and can be manufactured cheaply in large quantities.

SUMMARY OF THE INVENTION

It therefore is an object of the present invention to provide a breathable clothlike barrier having a controlled structure defensive composite.

Another object of the present invention is to provide a breathable clothlike barrier having a controlled structure defensive composite which is especially well suited for use as an outer cover or baffle in such disposable absorbent articles as diapers, sanitary napkins, and incontinent pads.

These and other objects will be apparent to one having ordinary skill in the art from a reading of the specification and claims which follow.

Accordingly, the present invention provides a breathable clothlike barrier which comprises a defensive composite comprising at least two layers:

A. a first layer which is a clothlike porous substrate having a first side and a second side, in which:
  said first layer has a nominal basis weight of at least about 10 g/m$^2$;
  the fibers comprising said first layer have an average fiber diameter in the range of from about 0.01 to about 10 microns; and
  each of substantially all of the pores at the surface of said first side of said first layer has a cross-sectional area of from about $6 \times 10^{-16}$ m$^2$ to about $2 \times 10^{-9}$ m$^2$; and B. a second layer joined to said first side of said first layer, which second layer comprises a continuous film of a poly(vinyl alcohol), in which:
  said film is not microporous in that it is substantially free of voids which connect the two surfaces of said film; and
  said film has an average thickness of (a) from about 3 to about 25 microns when the basis weight of said first layer is at least about 20 g/m$^2$ or (b) from about 8 to about 25 microns when the basis weight of said first layer is from about 10 to less than about 20 g/m$^2$;

wherein the first layer side of said second layer is intimately comingled with at least some of the fibers at the surface of said first side of said first layer, and said defensive composite has a water vapor transmission rate at 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

In certain preferred embodiments, the first layer is a clothlike fibrous substrate. In other preferred embodiments, the first layer is a nonwoven web, such as a meltblown web. In still other preferred embodiments, the breathable clothlike barrier includes a third layer which can be either a film similar to the second layer or a porous substrate similar to the first layer, and, in some embodiments, also includes a fourth layer which also can be either a film similar to the second layer or a porous substrate similar to the first layer.

DETAILED DESCRIPTION OF THE INVENTION

Figure 1:
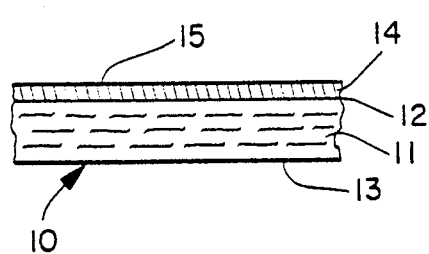
FIG. 1 is a diagrammatic representation of a cross-sectional view of the defensive composite required by the present invention; it represents the most general and most simple form of a breathable clothlike barrier coming within the scope of the present invention and is representative of the barrier prepared in Example 1.

As already noted, the breathable clothlike barrier of the present invention is especially well suited for use as an outer cover or baffle in such absorbent articles as disposable diapers, sanitary napkins, and incontinent pads. For this reason, the discussion herein focuses primarily on such uses. However, the barrier of the present invention can be employed in any product where water impermeability and water vapor permeability are either desired or necessary characteristics. Consequently, such discussion is not to be construed as in any way limiting either the spirit or scope of the present invention.

As used herein, the term "breathable clothlike barrier" means a clothlike material which is permeable to water vapor but which is impermeable to 0.9 percent by weight saline solution at a temperature of about 21 degrees C. for a period of at least one hour at a hydrostatic head of at least about 11.4 cm. The material is permeable to water vapor for the purposes of the present invention if it has a water vapor transmission rate at 37 degrees C. and about 50 percent relative humidity of from about 100 to about 5,000 g/m$^2$/24 hours.

The unique properties provided by the barrier of the present invention are derived from the presence of a bilayer composite, referred to herein for convenience as the defensive composite. The term "defensive" is used primarily in reference to the water impermeability of the barrier; that is, the composite is a "defense" against intrusion by liquid water from one side of the composite to the other.

The defensive composite comprises at least two layers:

A. a first layer which is a clothlike porous substrate having a first side and a second side, in which:
  said first layer has a nominal basis weight of at least about 10 g/m$^2$;
  the fibers comprising said first layer have an average fiber diameter in the range of from about 0.01 to about 10 microns; and
  each of substantially all of the pores at the surface of said first side of said first layer has a cross-sectional area of from about $6 \times 10^{-16}$ m$^2$ to about $2 \times 10^{-9}$ m$^2$; and B. A second layer joined to said first side of said first layer, which second layer comprises a continuous film of a poly(vinyl alcohol), in which: said film is not microporous in that it is substantially free of voids which connect the two surfaces of said film; and said film has an average thickness of (a) from about 3 to about 25 microns when the basis weight of said first layer is at least about 20 g/m$^2$ or (b) from about 8 to about 25 microns when the basis weight of said first layer is from about 10 to less than about 20 g/m$^2$;

wherein the first layer side of said second layer is intimately comingled with at least some of the fibers at the surface of said first side of said first layer, and said defensive composite has a water vapor transmission rate at 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

In general, the first layer can be any clothlike porous material as long as the requirements described herein for such material are met. Thus, the first layer can be a paper, apertured film or net, fibrillated film, woven or knitted fabric, or a nonwoven web, such as a meltblown, spunbonded, coformed, stichbonded, needle punched, or bonded carded web. A fibrous porous substrate is preferred, with a nonwoven web being more preferred. The most preferred nonwoven substrates are meltblown, coformed, and bonded carded webs. As a practical matter, the requirements of the present invention are most readily met by meltblown webs.

Clothlike porous substrates and methods for making them are well known in the art. By way of illustration only, examples of references teaching meltblowing, spunbonding, or coforming processes include U.S. Pat. Nos. 3,016,599, 3,755,527, 3,704,198, 3,849,241, 4,100,324, and 3,692,618, all of which are incorporated herein by reference.

The material out of which the first layer is made is not known to be critical. When the first layer is a fibrous substrate, the fibers preferably will be formed from a thermoplastic polymer, such as polyesters, polyamides, polyurethanes, polyolefins, combinations thereof, and the like. The polyolefins are the preferred thermoplastic polymers.

For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block polymers of two or more polyolefins (or two or more different polyolefin monomeric precursors) or one or more polyolefins and one or more nonpolyolefin polymers. Similarly, polymer blends can utilize two or more polyolefins or one or more polyolefins and one or more nonpolyolefin polymers. As a practical matter, homopolymers and copolymers and polymer blends involving only polyolefins are preferred, with homopolymers being most preferred.

Examples of polyolefins include polyethylene, polystyrene, poly(vinly chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

From the summary of the invention, it is seen that the first layer has limitations with respect to basis weight, fiber diameter, and pore size. It is these limitations, in conjunction with the requirements for the second layer and the interrelationship between the two layers, which has led to the designation of the defensive composite as a controlled structure. Thus, the term "controlled structure" refers to the structural limitations imposed on the defensive composite in accordance with the present invention.

It is important to keep in mind that the structural limitations described herein are important primarily because of the interrelationships between them. That is, the characteristics of the defensive composite described and claimed herein result not so much from the individual limitations but from the combination of them in any given composite. Stated differently, the characteristics of the defensive composite largely are a function of the basis weight, fiber diameters, and pore sizes of the first layer and the thickness of the second layer. This is not to minimize the significance of the construction of the first layer or the composition of the second layer. But, if significant deviations from such limitations are experienced, the best constructions and compositions may not yield a barrier having satisfactory barrier properties.

Turning now to the structural limitations of the first layer, such layer should have a basis weight of at least about 10 g/m$^2$, preferably at least about 20 g/m$^2$. Most preferably, the basis weight of the first layer will be at least about 25 g/m$^2$ in order to permit thinner second layers. Basis weight is significant because the sizes and uniformity of the pores at the surface of each side of the first layer in part are a function of the thickness of the layer. As a general rule, the pore size limitation is difficult to meet if the basis weight of the first layer is not at least about 10 g/m$^2$.

First layers having basis weights in the range of from about 10 to less than about 20 g/m$^2$ also are difficult to use in the construction of defensive composites. Such difficulty results to a large extent from a lack of pore size uniformity at the surface of the first side. Fortunately, the lack of pore size uniformity usually can be compensated for by employing thicker second layers.

Since higher basis weights typically will have a favorable effect on pore sizes, i.e., contribute to lower and also more uniform pore sizes, the only upper limitations on basis weight are practical considerations, such as cost, flexibility, hand, and related factors.

Realistically, basis weights greater than about 102 g/m$^2$ are seldom necessary, especially for such disposable absorbent articles as diapers, feminine napkins or pads, and incontinent pads.

Another parameter, and limitation, which contributes to pore sizes is the average diameter of the fibers comprising the first layer. In general, fiber diameters should be in the range of from about 0.01 to about 10 microns, preferably from about 0.01 to about 5 microns. As a practical matter, current nonwoven technology, and current meltblown technology in particular, yields fiber diameters in the range of from about 3 to about 5 microns under what are generally considered to be optimum conditions. However, it should be apparent that smaller fiber diameters will contribute significantly to smaller pore sizes. Consequently, the lower limit for the preferred range of fiber diameters still is 0.01 microns, even though such small diameters presently are not possible on an economical commercial scale.

It must be noted that the requirement regarding fiber diameters is more qualitative than quantitative. That is, it is not essential that all fibers be in the specified range. This concept is implicit in the use of the term "average fiber diameter" in relation to this requirement. It is important, however, that the fiber diameter distribution not be so wide or so skewed in favor of larger diameter fibers that the formation of the second layer is significantly adversely affected. While the continuous film which is the second layer need not be perfectly formed, those imperfections which may be present should not be of such a nature or magnitude that the defensive composite no longer can function satisfactorily as a barrier to liquid water.

It perhaps should be mentioned at this point that fiber diameters are largely process dependent, as is well known by those having ordinary skill in the art. That is, fiber diameters are affected by throughput, or the amount of polymer extruded through a given number of spinnerette orifices per unit time; polymer viscosity, which in turn is partly dependent upon extrusion temperature; extrusion pressure; die tip temperature; primary and secondary air temperatures; forming distance; and the like. For further information regarding any of these variables, reference should be made to the nonwoven process patents referred to earlier and incorporated herein by reference.

Finally, pore sizes at a surface of the first layer, expressed in terms of area, should be in the range of from about $6 \times 10^{-16}$ to about $2 \times 10^{-9}$ m$^2$, preferably in the range of from about $6 \times 10^{-16}$ to about $7 \times 10^{-10}$ m$^2$, and most preferably in the range of from about $6 \times 10^{-16}$ to about $1.8 \times 10^{-10}$ m$^2$. Because the second layer is joined to only one side of the first layer and, as discussed later, if formed in situ from a coating of an aqueous solution of the poly(vinyl alcohol) on the first side of the first layer, the pore size requirement applies only to the side adjacent to the second layer, i.e., the first side of the first layer. Realistically, however, the pore size ranges of the two sides of the first layer are likely to be very similar.

As with the fiber diameter requirement, the pore size limitation also is more qualitative than quantitative. This is the reason for the use of the term "substantially all of the pores." It is important to avoid the presence of very large pores since they prevent the formation of a continuous film which is the second layer. However, the term "continuous film" does not mean perfection, but only that the film is sufficiently free of defects so that the barrier property of the film is not significantly impaired. Consequently, all of the pores do not have to be within the specified range. If the number of pores within the specified range is sufficiently high, i.e., substantially all of the pores, then the pore size distribution of a porous substrate typically will be such that the presence of very large pores is avoided. This is especially true with nonwoven, e.g., meltblown, webs.

As already stated, the second layer is joined to said first side of said first layer, which second layer comprises a continuous film of a poly(vinyl alcohol), in which:

said film is not microporous in that it is substantially free of voids which connect the two surfaces of said film; and said film has an average thickness of (a) from about 3 to about 25 microns when the basis weight of said first layer is at least about 20 g/m$^2$ or (b) from about 8 to about 25 microns when the basis weight of said first layer is from about 10 to less than about 20 g/m$^2$;

It perhaps should be observed at this point that the present invention is unique in part because it permits the use of relatively thin second layers without sacrificing barrier properties. Thus, one goal of the present invention is to keep the second layer, as well as all other layers, relatively thin. Consequently, some experimentation may be required to determine the optimum performance of any given defensive composite in a cloth-like barrier intended for a particular application. However, undue experimentation will not be required if the guidelines described herein are followed.

An important aspect of the present invention is the fact that the poly(vinyl alcohol) film which comprises the second layer of the defensive composite is not a microporous film as that term has been used in the art. That is, the poly(vinyl alcohol) film utilized in the present invention does not have voids or micropores which connect the two surfaces of the film. In a microporous film, the interconnecting voids provide a pathway for the transport of water molecules from one surface to another, the driving force being the difference in relative humidities at the two surfaces. The poly(vinyl alcohol) film employed in the present invention, however, utilizes a different mechanism, namely: water molecules must be soluble in the film and capable of being transported by means of such solubility from one surface of the film to the other.

It may be noted that liquid water does not have to be in direct contact with the second layer in order for water vapor to be transported from one side of the defensive composite to the other. Water molecules are absorbed by the film, transported through it, and released on the other side, i.e., the side having the lower relative humidity. This movement of water molecules through the defensive composite is not impeded by the first layer since the first layer always will be more permeable to water vapor than the second layer.

In the event liquid water does contact the defensive composite, the second layer continues to absorb and transport water molecules to the exterior of the defensive layer. However, the second layer also prevents liquid water from penetrating the defensive composite. If for some reason the second layer is breached, the first layer offers some resistance to the passage of liquid water through it, thereby enhancing or supporting the barrier characteristics of the second layer.

Another point worth noting is that the liquid side of the composite can be either the first layer or the second layer; even though the second layer is formed from a water-soluble poly(vinyl alcohol), liquid water can be in direct contact with the second layer. Consequently, it is not necessary to have a protective layer of some kind over the surface of the second layer which is not adjacent to the first layer. As a practical matter, though, there can be excessive twisting or other distortion applied to the defensive composite during use which can contribute to abrasion or other damage to the integrity of the second layer. Such damage can result in a breach of the composite by liquid water. Thus, it may be desirable to employ a third layer to add structural strength to the composite. Such layer can be a nonwoven web, such as a spunbonded, meltblown or bonded carded web.

The permissible thickness range for the continuous film, or second layer, is partly dependent upon the basis weight of the first layer. When the basis weight of the first layer is at least about 20 g/m², the average thickness of the continuous film should be in the range of from about 3 to about 25 microns. When the basis weight of the first layer is from about 10 to less than about 20 g/m², however, the average thickness of the film should be from about 8 to about 25 microns. As already noted, when the first layer has a basis weight in the lower range, a greater average film thickness is required to compensate for the generally poor pore size uniformity which is present in thinner first layers.

It should be noted that average film thickness is involved, not maximum film thickness. Because of the inherent roughness of the surfaces of many clothlike porous substrates, and nonwoven webs in particular, film thickness typically varies over the area constituting the defensive composite. This necessitates dealing with average film thickness. Moreover, the average film thickness is an adequate measure of the amount of the continuous film which constitutes the second layer. Stated differently, some variability or imprecision in film thickness is acceptable since the barrier properties of the film do not appear to be extremely sensitive to film thickness.

A related problem is the difficulty of accurately measuring film thickness. For the purposes of the present invention, it is sufficient if film thickness is only estimated. A reasonable estimate of the thickness of a film can be made from the amount of add-on of the PVOH resin or PVOH composition if the density of the resin or composition is known. With the poly(vinyl alcohol) resins employed in the examples, it was found that each g/m² of add-on was approximately equivalent to 0.85 micron of film thickness.

As is well known in the art, poly(vinyl alcohol), from which the second layer is prepared, is a synthetic water-soluble polymeric material. There are, however, numerous grades of poly(vinyl alcohol), many of which have different solubility characteristics in water. For example, some grades are soluble in water at ambient temperature, while others are soluble in water only at elevated temperatures. At the present time, though, there are no known limitations with respect to the grade or nature of the poly(vinyl alcohol) employed in the preparation of the second layer.

Poly(vinyl alcohol), for convenience often referred to hereinafter as PVOH, is produced by the hydrolysis of poly(vinyl acetate). PVOH is available commercially in several grades which differ in degree of polymerization and degree of hydrolysis. In general, the degree of polymerization will vary from about 500 to about 2,500; the corresponding molecular weights are from about 22,000 to about 110,000. The degree of hydrolysis usually will vary from about 85 percent to essentially 100 percent (e.g., 99.7 percent minimum hydrolysis). In addition, some modified PVOH materials also are available, such as so-called tackified grades which are borated PVOH resins (see U.S. Pat. No. 3,135,648).

Typical of the commercially available PVOH resins are the VINOL ® resins available from Air Products and Chemicals, Inc., Polymer Chemicals, Allentown, Pa.

Preferably, the PVOH resin will have a relatively high degree of hydrolysis, typically essentially completely hydrolyzed, since such a resin does not require the use of a crosslinking agent.

Although resins having a lower degree of hydrolysis can be employed with satisfactory results, such resins may require the presence of a crosslinking agent in the aqueous solution of PVOH with which the first layer is coated, depending upon the use intended for the defensive composite, since such resins often are quite soluble in water at ambient temperature. However, inclusion of a crosslinking agent is not required, even for such resins.

One of the remarkable aspects of the present invention is the fact that such resins can be used to prepare satisfactory defensive composites. There are a number of clothlike porous substrates, meltblown webs in particular, which exhibit barrier properties with respect to liquid water. Such barrier properties, however, generally are insufficient to permit such porous substrates to serve by themselves as barrier having the properties associated with the defensive composites of the present invention. Nevertheless, such substrates, when joined with a continuous film of a water-soluble polymer as provided herein, yield composites having properties which exceed the sum of the properties of the individual components making up the composite. That is, there is a kind of synergy which results from the combination of a porous substrate having significant barrier properties with a continuous film of a water-soluble polymeric material as provided by the present invention. For some applications, the porous substrate permits the use of polymeric materials which are quite soluble in water at ambient temperature, as already observed. As a practical matter, however, it is preferred that such continuous film or second layer is substantially insoluble in water having a temperature less than about 50 degrees C.

Suitable crosslinking agents are those known in the art, such as glyoxal; formaldehyde; urea-formaldehydes; melamine-formaldehydes; metal compounds, such as cupric ammonium complexes, chromium complexes, organic titanates, and dichromates; and the like. When required, a crosslinking agent usually is employed in an amount in the range of from about 1 to about 5 percent by weight, based on the dry weight of PVOH, although higher or lower amounts can be employed, if desired.

In addition to the use of chemical crosslinking agents as discussed above, the PVOH film can be crosslinked by radiation, such as electron beam radiation, ultraviolet radiation, and the like. The formed PVOH film also can be crosslinked thermally by heating the film to a temperature in excess of 100 degrees C. The preferred temperature range is from about 120 to about 180 degrees C. In the preferred temperature range, the crosslinking time typically is about one hour. Thermal crosslinking is preferred over the use of a chemical crosslinking agent, especially when the breathable, multilayer, clothlike barrier is to be used in a disposable absorbent article such as a diaper, sanitary napkin, or incontinent pad.

Because flexibility of the breathable, multilayer, clothlike barrier often is a required characteristic, it may be either necessary or desirable to include a plasticizer in the PVOH film. Suitable plasticizers in general are any of the known plasticizers for PVOH, such as glycerol, the poly(oxyethylene) diols, pentaerythritol, 1,2,6-hexanetriol, sorbitol, formamide, urea, and the like. Glycerol has been found to be a particularly useful plasticizer and is preferred. Thus, a plasticizer can be present in an amount of from 0 to about 50 percent by weight, based on the dry weight of PVOH employed, although somewhat higher amounts perhaps can be used, depending on the grade of poly(vinyl alcohol) and the plasticizer. When employed, the plasticizer preferably will be present in an amount of from about 15 to about 25 percent by weight.

Some care must be exercised in the use of plasticizers, however. While plasticizers can increase film flexibility and enhance film formation, they also can adversely affect the liquid water barrier characteristics of the defensive composite, especially when used at unusually high levels. Thus, the plasticizer level in general should be kept to the minimum level which is consistent both with the film formation and flexibility requirements and the properties desired for the defensive composite.

As indicated hereinbefore, the PVOH is applied to a first side of the first layer as an aqueous solution. Application usually is made at ambient temperature and pressure, although such conditions are not mandatory. Indeed, any combination of temperature and pressure can be employed, although for reasons of economics and convenience, ambient temperature and pressure are preferred.

The concentration of PVOH in the solution is not known to be critical and usually is a matter of convenience. In practice, concentrations of from about 4 to about 12 percent by weight are typical. The preferred concentration range is from about 5 to about 8 percent by weight.

The method of application is not known to be critical and largely is a matter of convenience. Thus, the PVOH solution can be applied by spraying, dipping, brushing, doctor blade, roller, Meyer rod, and the like. The use of a roller coater with a Meyer rod works well and is preferred. In addition, a single coat or multiple coats can be applied. Moreover, if multiple coats are applied, the application solution does not have to be the same for each application. The several solutions can utilize different concentrations of PVOH, the presence of absence of such compounds as crosslinking agent and plasticizer, the presence or absence of other additives, or combinations of any of the foregoing variations.

The amount of PVOH present in the second layer typically will be in the range of from about 3 to about 15 g/m$^2$. Of course, lower or higher amounts can be employed, if desired.

After the aqueous solution of PVOH has been applied to the first layer, the resulting combination is dried by removing water, preferably at an elevated temperature. Upon drying, a continuous film of poly(vinyl alcohol) is formed which is contiguous with and tightly adherent to said first side of said first layer. Thus, the resulting second layer overlays and is joined to the first layer. If a subsequent layer is to be applied overlaying and joined to the resulting PVOH film or second layer, such application can be done before drying has been completed and is preferred when the subsequent layer is a porous nonwoven web since the PVOH has adhesive properties.

Finally, additives other than crosslinking agents and plasticizers can be incorporated into the PVOH film, if desired. Such additives include binders, extenders, fillers, pigments, dyes, defoamers, preservatives, fungicides, wetting agents, deodorants, fluorescent agents, latexes, fluorocarbons, water-repellent extenders, waxes, and the like. Incorporation is accomplished by simply dissolving or dispersing such additives in the aqueous coating solution.

As already stated, a third layer can be present. The third layer in general can be any porous substrate or a continuous film of a poly(vinyl alcohol). If the third layer, when present, is a porous substrate, the same criteria which apply to the first layer also apply to the third layer as well. When the third layer is a continuous film of a poly(vinyl alcohol) the criteria for the second layer apply. If a film, the third layer can be the same as or different from the second layer. Preferably, the third layer will be either a nonwoven web, such as a spunbonded or meltblown web, or a continuous film of a poly(vinyl alcohol). Finally, the third layer can be joined to either the second layer or to the second side of the first layer. When the third layer is a continuous film of a poly(vinyl alcohol) which is joined to the second layer, the amount of PVOH or PVOH composition in each of the second and third layers can be reduced to from about 2 to about 6 g/m$^2$. Of course, lower or higher amounts can be employed in either or both layers, if desired.

A fourth layer also can be present, if desired. The criteria for the fourth layer are the same as the criteria for the third layer. Moreover, additional layers can be added to the defensive composite of the present invention as desired. If present, such additional layers will be selected from the group consisting of a PVOH film and a porous substrate. The PVOH film will have characteristics similar to the second layer and the substrates will be similar to the first and third layers described hereinbefore.

It should be apparent to one having ordinary skill in the art that at least one layer in addition to the defensive composite must be clothlike if such additional layers are located on an external or outermost surface of the barrier. Thus, either one or both of the external barrier surfaces can be clothlike, depending upon the intended use. Furthermore, if only one surface is clothlike, that surface may face inwardly or outwardly.

For example, when the barrier is the outer cover of a disposable diaper, the clothlike surface should be the mother side. For rainwear applications, it may be preferred to have the clothlike surface of the barrier closest to the wearer, i.e., on the body side.

Although the various layers which comprise the breathable clothlike barriers of the present invention must be joined to each other, the method of joining is not critical. Indeed, any of the known methods of joining two sheets together can be employed. Such methods include thermal bonding, chemical or adhesive bonding, solvent bonding, ultrasonic bonding, laser bonding, needle punching, hydraulic entanglement, and the like. The term "joining" also is used herein to include the formation of one layer on another layer in situ.

The most general and most simple form of a breathable clothlike barrier coming within the scope of the present invention, i.e., the defensive composite, is illustrated diagrammatically by FIG. 1. In FIG. 1, composite 10 comprises first layer 11 which is a clothlike porous substrate having first side 12 and second side 13. To first side 12 is joined second layer 14 which is a continuous film of a poly(vinyl alcohol). In most applications, the liquid side surface will be surface 15.

To obtain the composite of FIG. 1, a clothlike porous substrate, such as a meltblown web, is coated with an aqueous solution of a poly(vinyl alcohol). Upon drying the coating, the composite of FIG. 1 is obtained.

FIGS. 2–13, inclusive, represent certain preferred embodiments, including the embodiments as prepared in the examples.

Figure 2:
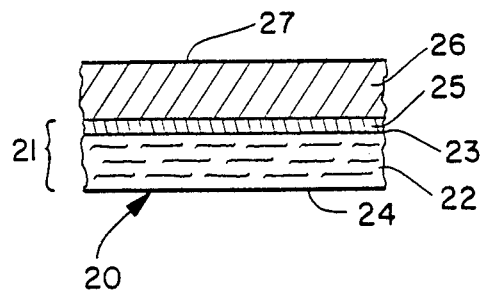
FIGS. 2-13, inclusive, are diagrammatic representations of cross-sectional views of various preferred embodiments of the present invention. The embodiment of FIG. 3 is representative of the barrier prepared in Example 2.

Turning now to FIG. 2, barrier 20, which includes defensive composite 21, comprises first layer 22 which is a clothlike porous substrate, such as a meltblown web, having a first side 23 and a second side 24, second layer 25 which is a continuous film of a poly(vinyl alcohol) joined to the first side 23 of first layer 22, and third layer 26 which is a porous substrate, such as a spunbonded web, which is joined to the second layer 25. The liquid side surface usually will be surface 27. The barrier 20 represented by FIG. 2 is the defensive composite 10 of FIG. 1 having a third layer joined to the second layer. The barrier is readily prepared as described for the barrier of FIG. 1, except that the third layer is placed over the second layer before the drying step. The PVOH employed to make the second layer usually will be plasticized with, for example, from about 15 to about 25 percent by weight, based on the dry weight of the PVOH resin, of glycerol. The concentration of PVOH in the coating solution typically will be from about 4 to about 10 percent by weight. The dry weight add-on of the PVOH or PVOH compositin to the meltblown web ordinarily is from about 3 to about 15 g/m$^2$.

Figure 3:
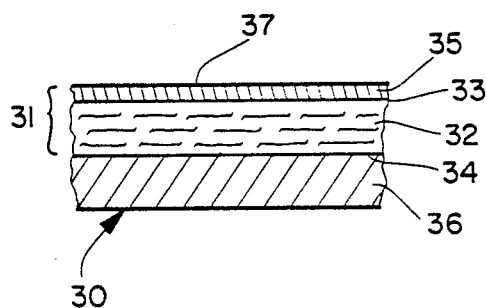

The barrier of FIG. 3 differs from that of FIG. 2 only in the location of the third layer. In FIG. 3, barrier 30, which includes defensive composite 31, comprises first layer 32 which is a porous substrate having a first side 33 and a second side 34, second layer 35 which is a continuous film of a poly(vinyl alcohol) joined to the first side 33 of a first layer 32, and third layer 36 which is joined to the second side 34 of the first layer 32. The liquid side surface usually will be surface 37. Barrier 30 is readily prepared by coating an existing laminate composed of the first and third layers, followed by drying the coated laminate, or by joining a third layer material to the second side of the first layer of an existing defensive composite.

Figure 4:
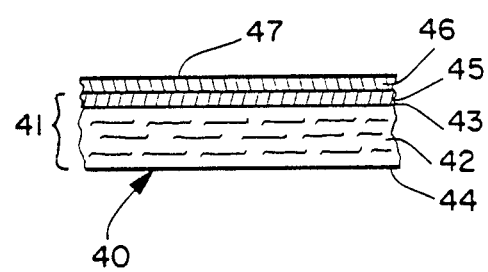

The barrier 40 of FIG. 4 is the barrier of FIG. 1 to which a third layer has been added. Thus, barrier 40, which includes defensive composite 41, comprises first layer 42 which is a porous substrate having a first side 43 and a second side 44, second layer 45 joined to said first side 43 of first layer 42, and third layer 46 joined to second layer 45, each of said second and third layers being a continuous film of a poly(vinyl alcohol). The liquid side surface typically is surface 47. Because the barrier 40 includes two PVOH film layers, the add-on for each layer typically can be reduced to from about 2 to about 6 g/m$^2$. In preparing the barrier 40, a second coating of the same or a different PVOH coating solution is applied to the second layer of an existing defensive composite, followed by a drying step.

Figure 5:
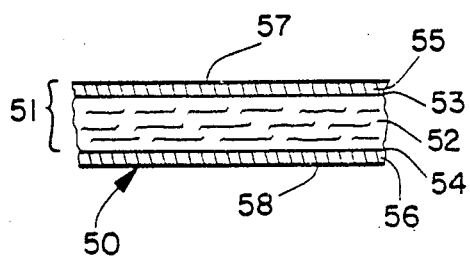

Barrier 50 of FIG. 5 is similar to that of FIG. 4, except that the third layer is joined to the second side of the first layer, rather than to the second layer. Hence, barrier 50, which includes defensive composite 51, comprises first layer 52 which is a porous substrate having a first side 53 and a second side 54, second layer 55 joined to the first side 53 of the first layer 52, and third layer 56 joined to the second side of the first layer 52. The fluid side surface can be either surface 57 or surface 58. Except for the location of the third layer, barrier 50 can be prepared in the same manner as described for barrier 40 of FIG. 4. With the proper equipment, the first layer material can be coated simultaneously on both sides with PVOH solutions and then dried to give barrier 50.

Figure 6:
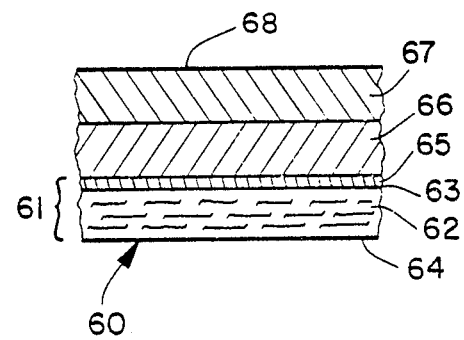
Figure 7:
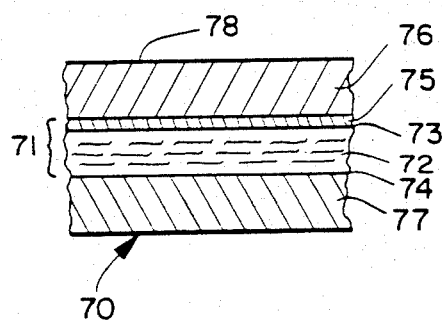

Upon adding a fourth layer which is a porous substrate to the barrier 20 of FIG. 2, the barriers of FIGS. 6 and 7 result. In FIG. 6, barrier 60, which includes defensive composite 61, comprises first layer 62 which is a porous substrate having a first side 63 and a second side 64, second layer 65 joined to the first side 63 of the first layer 62, third layer 66 joined to the second layer 65, and fourth layer 67 joined to the third layer 66. The second layer 65 is a continuous film of a poly(vinyl alcohol) and the third and fourth layers are porous substrates. Barrier 70 of FIG. 7 differs from barrier 60 of FIG. 6 only in the location of the fourth layer; in FIG. 7, the fourth layer is joined to the second side 74 of the first layer 72. The liquid side surfaces of barriers 60 and 70 of FIGS. 6 and 7, respectively, ordinarily will be surfaces 68 and 78, respectively. The barriers can be prepared by joining the fourth layer to the appropriate surface of the barrier of FIG. 2. It is not necessary, however, to begin with the barrier of FIG. 2. For example, barrier 60 also can be prepared by forming a laminate of the third and fourth layer materials, coating the remaining side of the third layer with the PVOH solution, joining the coated laminate with the first layer material, and drying the resulting product. If desired, the first layer material can be coated with the PVOH solution. The resulting defensive composite precursor then is joined with the third layer-fourth layer laminate and dried.

Figure 8:
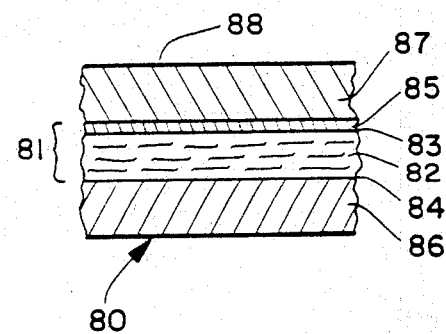
Figure 9:
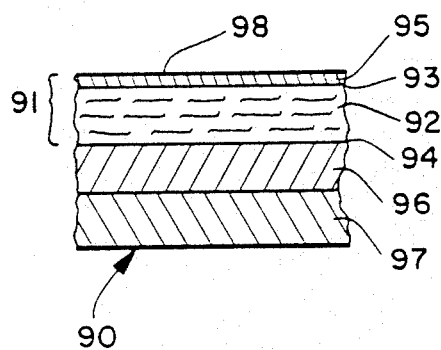

In a similar fashion, the barriers of FIGS. 8 and 9 are the barrier of FIG. 3 to which a porous substrate fourth layer has been added. Barrier 80 of FIG. 8, which includes defensive composite 81, comprises first layer 82 which is a porous substrate having a first side 83 and a second side 84, second layer 85 which is a continuous film of a poly(vinyl alcohol) joined to the first side 83 of first layer 82, third layer 86 which is a porous substrate joined to the second side 84 of the first layer 82, and fourth layer 87 which is a porous substrate joined to the second layer 85.

In FIG. 9, barrier 90, which includes defensive composite 91, comprises first layer 92 which is a porous substrate having a first side 93 and a second side 94, second layer 95 which is a continuous film of a poly(vinyl alcohol) joined to the first side 93 of first layer 92, third layer 96 which is a porous substrate joined to the second side 94 of the first layer 92, and fourth layer 97 which is a porous substrate joined to third layer 96. The liquid side surfaces of the barriers of FIGS. 8 and 9 typically will be surfaces 88 and 98, respectively.

The barriers of FIGS. 8 and 9 are readily prepared by means of the procedures already described in relation to the preceding figures. Such procedures also apply to the barriers of FIGS. 10-13, inclusive, described below.

Figure 10:
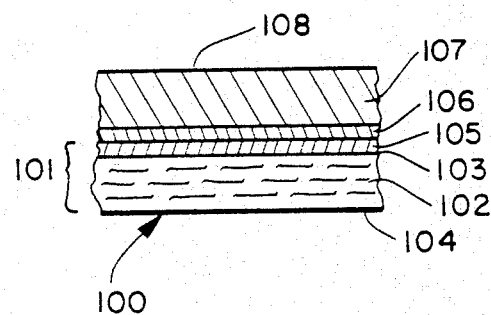

The barrier of FIG. 10 can be considered to be derived from the barrier of FIG. 4 by joining a fourth layer which is a porous substrate to the third layer of barrier 40. Thus, barrier 100, which includes defensive composite 101, comprises first layer 102 which is a porous substrate having a first side 103 and a second side 104, second layer 105 which is a continuous film of a poly(vinyl alcohol) joined to the first side 103 of first layer 102, third layer 106 joined to the second layer 105, the third layer also being a continuous film of a poly(vinyl alcohol), and fourth layer 107 which is a porous substrate joined to the third layer 106. The liquid side surface normally will be surface 108.

Figure 11:
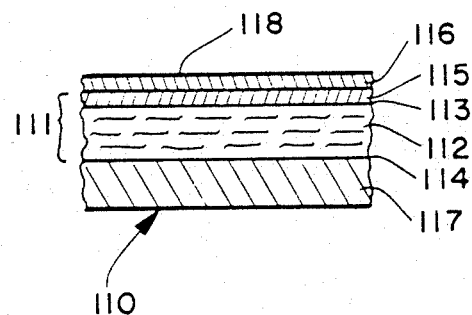

In an analogous manner, the barrier of FIG. 11 also can be considered to be derived from the barrier of FIG. 4. Thus, barrier 110, which includes defensive composite 111, comprises first layer 112 which is a porous substrate having a first side 113 and a second side 114, second layer 115 which is a continuous film of poly(vinyl alcohol) joined to the first side 113 of the first layer 112, third layer 116 which is a continuous film of a poly(vinyl alcohol) joined to the second layer 115, and fourth layer 117 which is a porous substrate joined to the second side 114 of the first layer 112, Surface 118 usually will be the liquid side surface.

Figure 12:
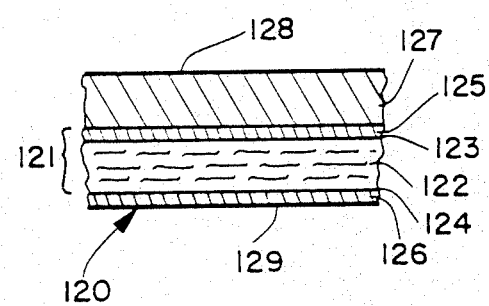

The addition of a porous substrate fourth layer to the barrier of FIG. 5 gives barrier 120 of FIG. 12. Barrier 120, which includes defensive composite 121, comprises first layer 122 which is a porous substrate having a first side 123 and a second side 124, second layer 125 which is a continuous film of a poly(vinyl alcohol) joined to the first side 123 of the first layer 122, third layer 126 which is a continuous film of a poly(vinyl alcohol) joined to the second side 124 of the first layer 122, and fourth layer 127 which is a porous substrate joined to second layer 122. The liquid side surface for most applications will be surface 128.

Figure 13:
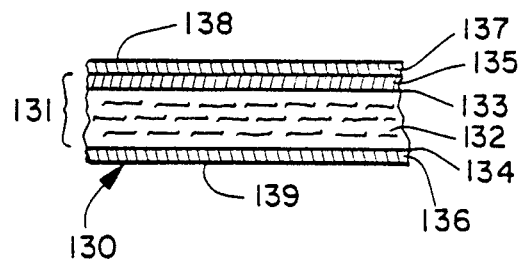

If the fourth layer of the barrier of FIG. 12 is replaced with a layer which is a continuous film of a poly(vinyl alcohol) the barrier 130 of FIG. 13 results. Thus, barrier 130, which includes defensive composite 131, comprises first layer 132 which is a porous substrate having a first side 133 and a second side 134, second layer 135 which is a continuous film of a poly(vinyl alcohol) joined to the first side 133 of the first layer 132, third layer 136 which is a continuous film of a poly(vinyl alcohol) joined to the second side 134 of the first layer 132, and fourth layer 137 which is a continuous film of a poly(vinyl alcohol) joined to the second layer 135. The liquid side surface typically will be surface 138.

The present invention is further described by the examples which follow, illustrating several preferred embodiments of the present invention. Such examples are not to be construed as in any way limiting either the spirit or scope of the present invention.

In the examples, the water vapor transmission rate was determined in accordance with ASTM Method E 96-80, Standard Test Methods for Water Vapor Transmission of Materials, Procedure 12. The apparatus employed was a Vapometer (Catalog No. 68-1, Thwing-Albert Instrument Company, Philadelphia, Pa.). The apparatus consisted of a two-inch (about 5.1-cm) deep aluminum cup having a flanged top with a neoprene rubber gasket. The inner diameter of the flange was 2.5 inches (about 6.4 cm). About 100 ml of water was added to the cup and a sample of the breathable barrier to be tested was sealed mechanically over the open end of the cup and weighed. The sample-cup assembly was placed in an oven at 37 degrees C. and about 50 percent relative humidity. Periodic weighings of the sample-cup assembly permitted calculation of the water vapor transmission rate (WTVR).

The effectiveness of the breathable clothlike barrier as a barrier to liquid water was measured by INDA Standard Test 80.7-70 (82), INDA Standard Test for Saline Repellency of Nonwovens, often referred to as the Mason Jar Test. The test liquid was 0.9 percent by weight saline solution.

EXAMPLE 1

An approximately eight percent by weight aqueous solution of a poly(vinyl alcohol) was prepared by dispersing the resin in water at ambient temperature containing 1 percent by weight glycerol and heating the mixture at about 96 degrees C. with moderate agitation until the resin dissolved. The poly(vinyl alcohol) employed was VINOL ® 125 (Air Products and Chemicals, Inc., Polymer Chemicals, Allentown, Pa.). According to information supplied by the manufacturer, the resin was in excess of 99.3 percent hydrolyzed and a 4 percent by weight aqueous solution of the resin at 20 degrees C. had a viscosity of 26–30 cps. The amount of glycerol present was equivalent to about 12 percent by weight, based on the amount of PVOH resin; on a dry weight basis, the composition of the PVOH composition was 11 percent glycerol and 89 percent PVOH resin. The resulting solution then was allowed to cool to ambient temperature.

The above PVOH solution was applied by means of a No. 22 Meyer rod to a sample of a polypropylene meltblown nonwoven web having a nominal basis weight of 25 g/m$^2$. The coated sample was air dried at 140 degrees C. for two minutes. The level of add-on of the PVOH composition was 5.3 g/m$^2$. The coated sample passed the Mason Jar Test and gave a water vapor transmission rate of 2392 g/m$^2$/24 hours.

Figure 14:
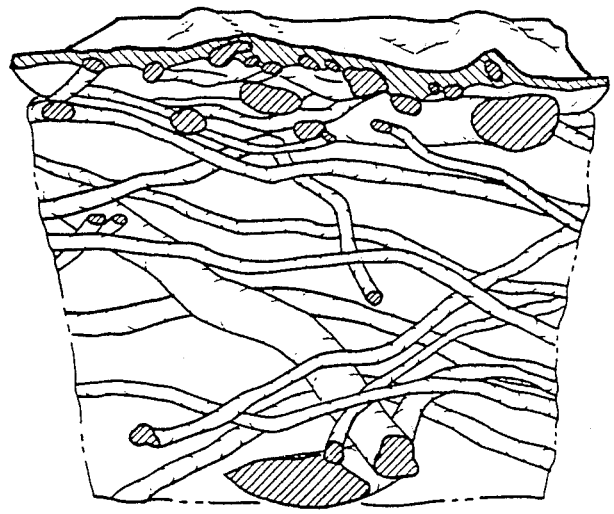
FIGS. 14 and 15 are representations of cross-sectional view scanning electron micrographs of a defensive composite as required by the present invention.
Figure 15:
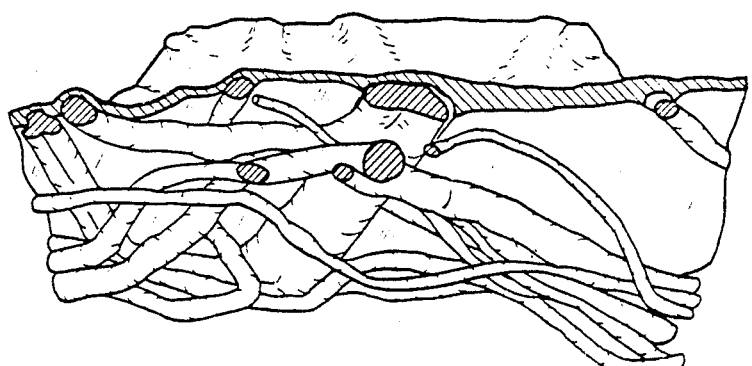

A polypropylene meltblown web coated once as described in Example 1 was examined in cross-section by scanning electron microscopy. FIGS. 14 and 15 are representations of the micrographs obtained at a magnification of 1000X. The very thin nature of the resulting film and the comingling phenomenon described earlier are readily apparent.

EXAMPLE 2

The procedure of Example 1 was repeated, except that the PVOH solution contained six percent by weight of the PVOH resin and did not contain glycerol and the nonwoven web was a 14-inch wide thermally bonded carded web-meltblown web composite, with the coating being applied to the meltblown side of the composite. The composite was prepared by forming the meltblown web directly onto the bonded carded web; the composite had a delamination strength of 75 g/in. Both the bonded carded web and the meltblown web were composed of polypropylene fibers. The nominal basis weight of the bonded carded web was about 22 g/m$^2$ and that of the meltblown web was about 25 g/m$^2$.

The PVOH add-on was about 5 g/m$^2$. The coated composite passed the Mason Jar Test and several samples gave water vapor transmission rates in the range of 1500–1600 g/m$^2$/24 hours.

The external layer of the bonded carded web was soft and clothlike, and imparted additional strength to the barrier. The fiber diameters of the meltblown web were in the range of from about 5 to about 8 microns. Pore sizes of the meltblown web were in the range of from about $8 \times 10^{-11}$ to about $5 \times 10^{-10}$ m$^2$.

EXAMPLE 3

The procedure of Example 2 was repeated, except that the porous substrate was a polypropylene meltblown web having a nominal basis weight of 25 g/m$^2$ and the coated sample was air dried overnight at ambient temperature. Pore sizes of the meltblown web were substantially in the range of from about $8 \times 10^{-11}$ to about $1.8 \times 10^{-10}$ m$^2$.

The PVOH add-on was 3.5 g/m$^2$. The coated sample passed the Mason Jar Test.

EXAMPLE 4

The procedure of Example 3 was repeated, except that the meltblown web had a nominal basis weight of 17 g/m², the pore sizes of the web were substantially in the range of from about $2 \times 10^{-11}$ to about $3 \times 10^{-10}$ m², and the PVOH add-on was 7 g/m². The coated sample failed the Mason Jar Test.

The procedure was repeated to give a PVOH add-on of 10 g/m². This time, the performance of the coated sample in the Mason Jar Test was marginal. Thus, when the basis weight of the first layer is less than about 20 g/m², the thickness of the second layer needs to be at least about 8 microns in order to have sufficient barrier properties with respect to liquids.

EXAMPLE 5

The procedure of Example 4 was repeated, except that three meltblown webs were employed having nominal basis weights of 10, 27, and 34 g/m², respectively. The amount of PVOH present in the film on the meltblown web having a nominal basis weight of 10 g/m² was about 4.5 g/m². For each of the other two coated samples, the film add-on was about 2.5 g/m². The pore size of the webs were in the same range as those of the web of Example 4. All of the coated samples failed the Mason Jar Test, demonstrating the need for a second layer thickness of at least about 3 microns when the basis weight of the first layer is at least about 20 g/m².

Having thus described the present invention, numerous changes and modifications thereof will be apparent to those having ordinary skill in the art without departing from either the spirit or the scope of the invention. For example, numerous barriers other than those illustrated by FIGS. 3–16, inclusive, can be constructed. Moreover, the characteristics given as representative of the various layers of the barriers of the figures can be altered as desired.

What is claimed is:

1. A breathable clothlike barrier which comprises a defensive composite comprising at least two layers:
   A. a first layer which is a clothlike porous substrate having a first side and a second side, in which:
      said first layer has a nominal basis weight of at least about 10 g/m²;
      the fibers comprising said first layer have an average fiber diameter in the range of from about 0.01 to about 10 microns; and
      each of substantially all of the pores at the surface of said first side of said first layer has a cross-sectional area of from about $6 \times 10^{-16}$ m² to about $2 \times 10^{-9}$ m²; and
   B. a second layer joined to said first side of said first layer, which second layer comprises a continuous film of a poly(vinyl alcohol), in which:
      said film is not microporous in that it is substantially free of voids which connect the two surfaces of said film; and
      said film has an average thickness of (a) from about 3 to about 25 microns when the basis weight of said first layer is at least about 20 g/m² or (b) from about 8 to about 25 microns when the basis weight of said first layer is from about 10 to less than about 20 g/m²;
   wherein the first layer side of said second layer is intimately comingled with at least some of the fibers at the surface of said first side of said first layer, and said defensive composite has a water vapor transmission rate at 37 degrees C. and about 50 percent relative humidity of from about 100 to about 5,000 g/m²/24 hours and is impermeable to 0.9 percent by weight saline solution at about 21 degrees C. for a period of at least about one hour at a hydrostatic head of at least about 11.4 cm.

2. The breathable clothlike barrier of claim 1, in which said film is substantially insoluble in water having a temperature less than about 50 degrees C.

3. The breathable clothlike barrier of claim 1, in which said first layer is a fibrous substrate.

4. The breathable clothlike barrier of claim 3, in which said fibrous substrate is a nonwoven web.

5. The breathable clothlike barrier of claim 4, in which said nonwoven web is a meltblown web.

6. The breathable clothlike barrier of claim 5, in which said meltblown web is composed of polyolefin fibers.

7. The breathable clothlike barrier of claim 6, in which said polyolefin is polypropylene.

8. The breathable clothlike barrier of claim 5, in which said meltblown web is composed of fibers having diameters in the range of from about 0.01 to about 5 microns.

9. The breathable clothlike barrier of claim 5, in which each of substantially all of the pores of said meltblown web has a cross-sectional area of from about $6 \times 10^{-16}$ to about $7 \times 10^{-10}$ m².

10. The breathable clothlike barrier of claim 5, in which each of substantially all of the pores of said meltblown web has a cross-sectional area of from about $6 \times 10^{-16}$ to about $1.8 \times 10^{-10}$ m².

11. The breathable clothlike barrier of claim 5, in which the basis weight of said meltblown web is at least about 20 g/m².

12. The breathable clothlike barrier of claim 5, in which the basis weight of said meltblown web is at least about 25 g/m².

13. The breathable clothlike barrier of claim 1, in which said breathable clothlike barrier includes a third layer which is a porous substrate.

14. The breathable clothlike barrier of claim 13, in which said porous substrate is a fibrous substrate.

15. The breathable clothlike barrier of claim 14, in which said fibrous substrate is a nonwoven web.

16. The breathable clothlike barrier of claim 15, in which said third layer is joined to said second side of said first layer.

17. The breathable clothlike barrier of claim 15, in which said third layer is joined to said second layer.

18. The breathable clothlike barrier of claim 15, in which said nonwoven web is a meltblown web.

19. The breathable clothlike barrier of claim 18, in which said third layer is joined to said second side of said first layer.

20. The breathable clothlike barrier of claim 18, in which said third layer is joined to said second layer.

21. The breathable clothlike barrier of claim 15, in which said nonwoven web is a spunbonded web.

22. The breathable clothlike barrier of claim 21, in which said third layer is joined to said second side of said first layer.

23. The breathable clothlike barrier of claim 21, in which said third layer is joined to said second layer.

24. The breathable clothlike barrier of claim 1, in which said breathable clothlike barrier includes a third layer which comprises a continuous film of a poly(vinyl alcohol), in which:
   said film is not microporous in that it is substantially free of voids which connect the two surfaces of said film; and said film has an average thickness of from about 3 to about 250 microns.

25. The breathable clothlike barrier of claim 24, in which said film is substantially insoluble in water having a temperature less than about 50 degrees C.

26. The breathable clothlike barrier of claim 24, in which said third layer is joined to said second side of said first layer.

27. The breathable clothlike barrier of claim 24, in which said third layer is joined to said second layer.

28. The breathable clothlike barrier of claim 13, in which said breathable clothlike barrier includes a fourth layer which is a porous substrate.

29. The breathable clothlike barrier of claim 28, in which said fourth layer is a nonwoven web.

30. The breathable clothlike barrier of claim 14, in which said breathable clothlike barrier includes a fourth layer which is a porous substrate.

31. The breathable clothlike barrier of claim 30, in which said fourth layer is a nonwoven web.

32. The breathable clothlike barrier of claim 15, in which said breathable clothlike barrier includes a fourth layer which is a porous substrate.

33. The breathable clothlike barrier of claim 32, in which said fourth layer is a nonwoven web.

34. The breathable clothlike barrier of claim 24, in which said breathable clothlike barrier includes a fourth layer which is a porous substrate.

35. The breathable clothlike barrier of claim 34, in which said fourth layer is a nonwoven web.

36. The breathable clothlike barrier of claim 35, in which said fourth layer is joined to said first side of said first layer.

37. The breathable clothlike barrier of claim 36, in which said fourth layer is joined to said third layer.

38. The breathable clothlike barrier of claim 13, in which said breathable clothlike barrier includes a fourth layer which comprises a continuous film of a poly(vinyl alcohol), in which:
    said film is not microporous in that it is substantially free of voids which connect the two surfaces of said film; and
    said film has an average thickness of from about 3 to about 250 microns.

39. The breathable clothlike barrier of claim 38, in which said film is substantially insoluble in water having a temperature less than about 50 degrees C.

40. The breathable clothlike barrier of claim 14, in which said breathable clothlike barrier includes a fourth layer which comprises a continuous film of a poly(vinyl alcohol), in which:
    said film is not microporous in that it is substantially free of voids which connect the two surfaces of said film; and
    said film has an average thickness of from about 3 to about 250 microns.

41. The breathable clothlike barrier of claim 40, in which said film is substantially insoluble in water having a temperature less than about 50 degrees C.

42. The breathable clothlike barrier of claim 15, in which said breathable clothlike barrier includes a fourth layer which comprises a continuous film of a poly(vinyl alcohol), in which:
    said film is not microporous in that it is substantially free of voids which connect the two surfaces of said film; and
    said film has an average thickness of from about 3 to about 250 microns.

43. The breathable clothlike barrier of claim 42, in which said film is substantially insoluble in water having a temperature of less than about 50 degrees C.

44. The breathable clothlike barrier of claim 24, in which said breathable clothlike barrier includes a fourth layer which comprises a continuous film of a poly(vinyl alcohol), in which:
    said film is not microporous in that it is substantially free of voids which connect the two surfaces of said film; and
    said film has an average thickness of from about 3 to about 250 microns.

45. The breathable clothlike barrier of claim 44, in which said film is substantially insoluble in water having a temperature of less than about 50 degrees C.

46. A disposable absorbent article having an outer cover or baffle which is the breathable clothlike barrier of claim 1.

47. A disposable absorbent article having an outer cover or baffle which is the breathable clothlike barrier of claim 13.

48. A disposable absorbent article having an outer cover or baffle which is the breathable clothlike barrier of claim 15.

49. A disposable absorbent article having an outer cover or baffle which is the breathable clothlike barrier of claim 24.

50. A disposable absorbent article having an outer cover or baffle which is the breathable clothlike barrier of claim 42.

51. A disposable absorbent article having an outer cover or baffle which is the breathable clothlike barrier of claim 44.

52. A disposable diaper having an outer cover which is the breathable clothlike barrier of claim 1.

53. A disposable diaper having an outer cover which is the breathable clothlike barrier of claim 13.

54. A disposable diaper having an outer cover which is the breathable clothlike barrier of claim 15.

55. A disposable diaper having an outer cover which is the breathable clothlike barrier of claim 24.

56. A disposable diaper having an outer cover which is the breathable clothlike barrier of claim 42.

57. A disposable diaper having an outer cover which is the breathable clothlike barrier of claim 44.

58. A disposable sanitary napkin having a baffle which is the breathable clothlike barrier of claim 1.

59. A disposable sanitary napkin having a baffle which is the breathable clothlike barrier of claim 13.

60. A disposable sanitary napkin having a baffle which is the breathable clothlike barrier of claim 15.

61. A disposable sanitary napkin having a baffle which is the breathable clothlike barrier of claim 24.

62. A disposable sanitary napkin having a baffle which is the breathable clothlike barrier of claim 42.

63. A disposable sanitary napkin having a baffle which is the breathable clothlike barrier of claim 44.

64. A disposable continent pad having an outer cover which is the breathable clothlike barrier of claim 1.

65. A disposable incontinent pad having an outer cover which is the breathable clothlike barrier of claim 13.

66. A disposable incontinent pad having an outer cover which is the breathable clothlike barrier of claim 15.

67. A disposable incontinent pad having an outer cover which is the breathable clothlike barrier of claim 24.

68. A disposable incontinent pad having an outer cover which is the breathable clothlike barrier of claim 42.

69. A disposable incontinent pad having an outer cover which is the breathable clothlike barrier of claim 44.

* * * * *